United States Patent
Worrall et al.

(10) Patent No.: US 6,695,978 B2
(45) Date of Patent: Feb. 24, 2004

(54) MONO-, OLIGO- AND POLYMERS OF BENZO[B]THIOPHENE AND 2,2'-BISBENZO[B]THIOPHENE AND THEIR USE AS CHARGE TRANSPORT MATERIALS

(75) Inventors: Christopher Worrall, Northwich (GB); Martin Heeney, Southampton (GB); Steven Tierney, Southampton (GB); Louise Diane Farrand, Blandford Forum (GB); Mark Giles, Southampton (GB); Marcus Thompson, Fordingbridge (GB); Maxim Shkunov, Southampton (GB); David Sparrowe, Bournemouth (GB); Iain McCulloch, Kings Somborne (GB)

(73) Assignee: Merck Patent Gesellschaft mit beschraenkter Haftung, Darmstadt (DE)

(*) Notice: Subject to any disclaimer, the term of this patent is extended or adjusted under 35 U.S.C. 154(b) by 0 days.

(21) Appl. No.: 10/255,936

(22) Filed: Sep. 27, 2002

(65) Prior Publication Data

US 2003/0085381 A1 May 8, 2003

(30) Foreign Application Priority Data

Sep. 29, 2001 (EP) .............................................. 01123509

(51) Int. Cl.$^7$ ................................................ C09K 19/32
(52) U.S. Cl. ............................ 252/299.62; 252/299.61; 549/32; 549/61; 549/70
(58) Field of Search ....................... 252/299.01, 299.62, 252/299.61, 299.6; 549/1, 29, 30, 32, 61, 70

(56) References Cited

U.S. PATENT DOCUMENTS

| 5,198,153 A | 3/1993 | Angelopoulos et al. |
| 5,892,244 A | 4/1999 | Tanaka et al. |
| 5,998,804 A | 12/1999 | Suh et al. |

FOREIGN PATENT DOCUMENTS

| DE | 195 04 224 | 8/1995 |
| EP | 0 261 712 | 3/1988 |
| EP | 0 528 662 | 2/1993 |
| EP | 0 889 350 | 1/1999 |
| WO | WO 93/22397 | 11/1993 |
| WO | WO 95/22586 | 8/1995 |
| WO | WO 96/21659 | 7/1996 |
| WO | WO 97/00600 | 1/1997 |
| WO | WO 00/79617 | 12/2000 |

*Primary Examiner*—Mark F. Huff
*Assistant Examiner*—Jennifer R Sadula
(74) *Attorney, Agent, or Firm*—Millen, White, Zelano, Branigan, P.C.

(57) ABSTRACT

Conjugated mono-, oligo- and polymers of benzo[b]thiophene and bisbenzo[b]thiophene are useful as semiconductors or charge transport materials in optical, electrooptical or electronic devices including field effect transistors, electroluminescent, photovoltaic and sensor devices.

30 Claims, No Drawings

MONO-, OLIGO- AND POLYMERS OF BENZO[B]THIOPHENE AND 2,2'-BISBENZO[B]THIOPHENE AND THEIR USE AS CHARGE TRANSPORT MATERIALS

FIELD OF INVENTION

The invention relates to new conjugated mono-, oligo- and polymers of benzo[b]thiophene (thianaphthene) and bisbenzo[b]thiophene (bithianaphthene). The invention further relates to their use as semiconductors or charge transport materials in optical, electrooptical or electronic devices including field effect transistors, electroluminescent, photovoltaic and sensor devices. The invention further relates to field effect transistors and semiconducting components comprising the new mono-, oligo- and polymers.

BACKGROUND AND PRIOR ART

Organic materials have recently shown promise as the active layer in organic based thin film transistors and organic field effect transistors [see H. E. Katz, Z. Bao and S. L. Gilat, Acc. Chem. Res., 2001, 34, 5, 359]. Such devices have potential applications in smart cards, security tags and the switching element in flat panel displays. Organic materials are envisaged to have substantial cost advantages over their silicon analogues if they can be deposited from solution, as this enables a fast, large-area fabrication route.

The performance of the device is principally based upon the charge carrier mobility of the semiconducting material and the current on/off ratio, so the ideal semiconductor should have a low conductivity in the off state, combined with a high charge carrier mobility ($>1\times10^{-3}$ cm$^2$ V$^{-1}$ s$^{-1}$). In addition, it is important that the semiconducting material is relatively stable to oxidation, i.e., it has a high ionisation potential, as oxidation leads to reduced device performance.

A known compound which has been shown to be an effective p-type semiconductor for OFETs is pentacene [see S. F. Nelson, Y. Y. Lin, D. J. Gundlach and T. N. Jackson, Appl. Phys. Lett., 1998, 72, 1854]. When deposited as a thin film by vacuum deposition, it was shown to have carrier mobilities in excess of 1 cm$^2$ V$^{-1}$ s$^{-1}$ with very high current on/off ratios greater than $10^6$. However, vacuum deposition is an expensive processing technique that is unsuitable for the fabrication of large-area films.

Regular poly(3-hexylthiophene) has been reported with charge carrier mobility between $1\times10^{-5}$ and $4.5\times10^{-2}$ cm$^2$ V$^{-1}$ s$^{-1}$, but with a rather low current on/off ratio between 10 and $10^3$ [see Z. Bao et al., Appl. Pys. Lett. 1997, 78, 2184]. In general, poly(3-alkylthiophenes) show improved solubility and are able to be solution processed to fabricate large area films. However, poly(3-alkylthiophenes) have relatively low ionisation potentials and are susceptible to doping in air [see H. Sirringhaus et al., Adv. Solid State Phys. 1999, 39, 101].

It is an aim of the present invention to provide new materials for use as semiconductors or charge transport materials, which are easy to synthesize, have high charge mobility, good processibility and improved oxidative stability. Other aims of the invention are immediately evident to those skilled in the art from the following description.

The inventors have found that these aims can be achieved by providing new monomers, oligomers and polymers based on benzo[b]thiophene and 2,2'-bisbenzo[b]thiophene. Thus, benzo[b]thiophene (1) and 2,2'-bisbenzo[b]thiophene (2) are heterocycles that exhibit good conjugation and planarity. The introduction of alkyl chains R further improves solubility and solution processibility. Poly(2,5-benzo[b]thiophene) (3) and poly(2,2'-bisbenzo[b]thiophene) (4) exhibit a high degree of planarity in the backbone and strong interchain pi—pi-stacking interactions making them effective charge transport materials with high carrier mobilities. Also, the incorporation of alkyl substitutents R leads to good solubility and thus good solution processibility of the materials according to the present invention. Solution processing during device manufacture has the advantage over vaccum deposition of being a potentially cheaper and faster technique.

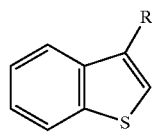

1

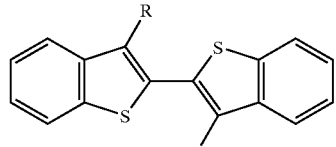

2

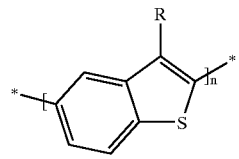

3

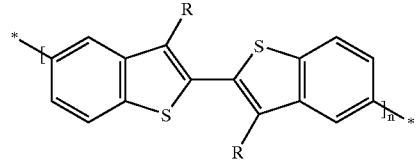

4

The synthesis of 2,2'-bisbenzo[b]thiophene (2) has been reported by Y. Fort et al., Tetrahedron, 1994, 50, 41, 11893. Unsubstituted poly(benzo[b]thiophene) has been reported via an electrochemical polymerisation (J. Electroanal. Chem. 2001, 510(1–2), 29–34, Makromol. Chem. Rapid Commun., 1987, 8, 325–9). The synthesis of substituted poly(2,5-benzo[b]thiophene) has not been reported. Moreover, mono- and poly(2,2'-bisbenzo[b]thiophenes) according to the present invention have not been reported.

A further aspect of the invention relates to reactive mesogens consisting of a central core comprising one or more benzo[b]thiophene or 2,2'-bisbenzo[b]thiophene units, and optionally comprising further unsaturated organic groups that form a conjugated system together with the (bis)benzo[b]thiophene units, said core being linked, optionally via a spacer group, to one or two polymerisable groups. The reactive mesogens can induce or enhance liquid crystal phases or are liquid crystalline themselves. They can be oriented in their mesophase and the polymerisable group can be polymerised or crosslinked in situ to form polymer films with a high degree of order, thus yielding improved semiconductor materials with high stability and high charge carrier mobility.

Grell et al., J. Korean Phys. Soc. 2000, 36(6), 331 suggest a reactive mesogen comprising a conjugated distyrylbenzene core with two reactive acrylate end groups as a model compound for molecular electronics. However, there is no disclosure of reactive mesogens of 2,2'-bisbenzo[b]thiophene.

A further aspect of the invention relates to liquid crystal polymers, in particular liquid crystal side chain polymers obtained from the reactive mesogens according to the present invention, which are then further processed, e.g., from solution as thin layers for use in semiconductor devices.

Definition of Terms

The terms 'liquid crystalline or mesogenic material' or 'liquid crystalline or mesogenic compound' means materials or compounds comprising one or more rod-shaped, lath-shaped or disk-shaped mesogenic groups, i.e., groups with the ability to induce liquid crystal phase behaviour. The compounds or materials comprising mesogenic groups do not necessarily have to exhibit a liquid crystal phase themselves. It is also possible that they show liquid crystal phase behaviour only in mixtures with other compounds, or when the mesogenic compounds or materials, or the mixtures thereof, are polymerised.

The term 'polymerisable' includes compounds or groups that are capable of participating in a polymerisation reaction, like radicalic or ionic chain polymerisation, polyaddition or polycondensation, and reactive compounds or reactive groups that are capable of being grafted, for example, by condensation or addition to a polymer backbone in a polymeranaloguous reaction.

The term 'film' includes self-supporting, i.e., free-standing, films that show more or less pronounced mechanical stability and flexibility, as well as coatings or layers on a supporting substrate or between two substrates.

SUMMARY OF THE INVENTION

One object of the invention are mono-, oligo- and polymers of formula I

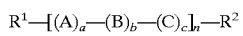

wherein

A and C are independently of each other —$CX^1$=$CX^2$—, —C≡C—, or optionally substituted arylene or heteroarylene, $X^1$ and $X^2$ are independently of each other H, F, Cl or CN, B is 2,5-benzo[b]thiophene or 2,2'-bisbenzo[b]thiophene that is optionally substituted with one or more groups R, R is H, halogen, straight chain, branched or cyclic alkyl with 1 to 20 C-atoms, which may be unsubstituted, mono- or polysubstituted by F, Cl, Br, I or CN, it being also possible for one or more non-adjacent $CH_2$ groups to be replaced, in each case independently from one another, by —O—, —S—, —NH—, —$NR^0$—, —$SiR^0R^{00}$—, —$SnR^0R^{00}$—, —CO—, —COO—, —OCO—, —OCO—O—, —S—CO—, —CO—S—, —CH=CH— or —C≡C— in such a manner that O and/or S atoms are not linked directly to one another, optionally substituted aryl or heteroaryl, or P—Sp—X, $R^1$ and $R^2$ have independently of each other one of the meanings of R, $R^0$ and $R^{00}$ are independently of each other H or alkyl with 1 to 12 C-atoms, P is a polymerisable or reactive group, Sp is a spacer group or a single bond, and X is —O—, —S—, —$OCH_2$—, —$CH_2O$—, —CO—, —COO—, —OCO—, —OCO—O—, —CO—$NR^0$—, —$NR^0$—CO—, —$OCH_2$—, —$CH_2O$—, —$SCH_2$—, —$CH_2S$—, —CH=CH—COO—, —OOC—CH=CH— or a single bond, a, b and c are independently of each other 0 or 1, with a+b+c>0, and wherein in at least one recurring unit [(A)$_a$—(B)$_b$—(C)$_c$] b is 1, and n is an integer ≧1, wherein the recurring units [(A)$_a$—(B)$_b$—(C)$_c$] can be identical or different, and with the proviso that in case n is 1 and a and c are 0, at least one of R, $R^1$ and $R^2$ is P—Sp—X.

Another object of the invention is the use of mono-, oligo- and polymers according to the invention as semiconductors or charge transport materials, in particular in optical, electrooptical or electronic devices, like for example components of integrated circuitry, field effect transistors (FET) for example as thin film transistors in flat panel display applications or for Radio Frequency Identification (RFID) tags, or in semiconducting components for organic light emitting diode (OLED) applications such as electroluminescent displays or backlights of, e.g., liquid crystal displays, for photovoltaic or sensor devices, as electrode materials in batteries, as photoconductors and for electrophotographic applications like electrophotographic recording.

Another object of the invention is a field effect transistor, for example as a component of integrated circuitry, as a thin film transistor in flat panel display applications, or in a Radio Frequency Identification (RFID) tag, comprising one or more mono-, oligo- or polymers according to the invention.

Another object of the invention is a semiconducting component, for example in OLED applications like electroluminescent displays or backlights of, e.g., liquid crystal displays, in photovoltaic or sensor devices, as electrode materials in batteries, as photoconductors and for electrophotographic applications, comprising one or more mono-, oligo- or polymers according to the invention.

Another object of the invention is a security marking or device comprising an RFID or ID tag or a FET according to the invention.

DETAILED DESCRIPTION OF THE INVENTION

The mono-, oligo- and polymers according to the present invention are especially useful as charge transport semiconductors in that they have high carrier mobilities. Particularly preferred are mono-, oligo-and polymers wherein the group B is substituted by one or more alkyl or fluoroalkyl groups. The introduction of alkyl and fluoroalkyl side chains to the group B improves the solubility and therefore the solution processibility of the inventive materials. Furthermore, the presence of fluoroalkyl side chains also renders the inventive materials effective as n-type semiconductors. The electron-withdrawing nature of the fluoroalkyl substituents will also lower the HOMO (highest occupied molecular orbital) further and result in a more stable material, which is less susceptible to oxidation.

Particularly preferred are mono-, oligo- and polymers comprising at least one group of formula I and at least one reactive group that is capable of a polymerisation or crosslinking reaction.

Further preferred are mono-, oligo- and polymers comprising at least one group of formula I that are mesogenic or liquid crystalline, in particular polymers of formula I forming calamitic phases, and reactive mesogens of formula I, comprising one or more groups P—Sp—X, forming calamitic phases.

In the oligo- and polymers of the present invention the recurring units $(A)_a$—$(B)_b$—$(C)_c$ in case of multiple occurrence can be selected of formula I independently of each other, so that an oligo- or polymer may comprise identical or different recurring units $(A)_a$—$(B)_b$—$(C)_c$. The oligo- and polymers thus include homopolymers and copolymers like for example statistically random copolymers, for example with a monomer sequence such as —A—B—C—C—B—A—B—, alternating copolymers, for example with a monomer sequence such as —A—B—C—A—B—C—, and block copolymers, for example with a monomer sequence such as —A—A—B—B—B—B—C—C—C—, wherein the groups A and C preferably form a conjugated system together with the group B.

Further preferred are mono-, oligo- and polymers comprising one or more recurring units $(A)_a$—$(B)_b$—$(C)_c$, wherein a=c=0 and b=1, very preferably consisting exclusively of such recurring units.

Further preferred are mono-, oligo- and polymers comprising one or more recurring units $(A)_a$—$(B)_b$—$(C)_c$, wherein b=c=1 and a=0, very preferably consisting exclusively of such recurring units.

Further preferred are mono-, oligo- and polymers comprising one or more recurring units $(A)_a$—$(B)_b$—$(C)_c$, wherein a=b=c=1, very preferably consisting exclusively of such recurring units.

Especially preferred are mono-, oligo- and polymers of formula I wherein B is selected of the following formulae

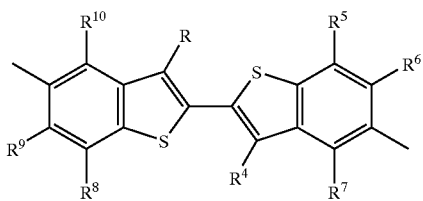

IIa

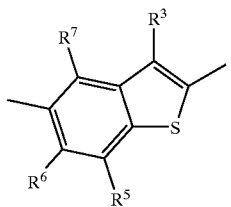

IIb wherein $R^3$ to $R^{10}$ independently of each other have one of the meanings of R in formula I.

Further preferred are mono-, oligo- and polymers of formula I wherein n is an integer from 1 to 5000, n is an integer from 2 to 5000, in particular from 20 to 1000, n is an integer from 2 to 5, n is 2 and one or both of $R^1$ and $R^2$ denote P—Sp—X, n is an integer from 1 to 15 and one or both of $R^1$ and $R^2$ denote P—Sp—X, n is an integer from 2 to 5000 and both $R^1$ and $R^2$ are not P—Sp—X, the molecular weight is from 5000 to 100000, $R^3$ and/or $R^4$ are different from H, $R^3$ and $R^4$ are independently of each other selected from $C_1$–$C_{20}$-alkyl that is optionally substituted with one or more fluorine atoms, $C_1$–$C_{20}$-alkenyl, $C_1$–$C_{20}$-alkynyl, $C_1$–$C_{20}$-alkoxy, $C_1$–$C_{20}$-thioether, $C_1$–$C_{20}$-silyl, $C_1$–$C_{20}$-ester, $C_1$–$C_{20}$-amino, $C_1$–$C_{20}$-fluoroalkyl, or optionally substituted aryl or heteroaryl, in particular $C_1$–$C_{20}$-alkyl or $C_1$–$C_{20}$-fluoroalkyl, $R^3$ and $R^4$ are independently of each other selected from $C_1$–$C_{20}$-alkyl that is optionally substituted with one or more fluorine atoms, $C_1$–$C_{20}$-alkenyl, $C_1$–$C_{20}$-alkynyl, $C_1$–$C_{20}$-alkoxy, $C_1$–$C_{20}$-thioether, $C_1$–$C_{20}$-silyl, $C_1$–$C_{20}$-ester, $C_1$–$C_{20}$-amino, $C_1$–$C_{20}$-fluoroalkyl, or optionally substituted aryl or heteroaryl, in particular $C_1$–$C_{20}$-alkyl or $C_1$–$C_{20}$-fluoroalkyl, and $R^5$ to $R^{10}$ are H, $R^5$ to $R^{10}$ are independently of each other selected from $C_1$–$C_{20}$-alkyl that is optionally substituted with one or more fluorine atoms, $C_1$–$C_{20}$-alkenyl, $C_1$–$C_{20}$-alkynyl, $C_1$–$C_{20}$-alkoxy, $C_1$–$C_{20}$-thioether, $C_1$–$C_{20}$-silyl, $C_1$–$C_{20}$-ester, $C_1$–$C_{20}$-amino, $C_1$–$C_{20}$-fluoroalkyl, and optionally substituted aryl or heteroaryl, $R^1$ and $R^2$ are independently of each other selected from $C_1$–$C_{20}$-alkyl that is optionally substituted with one or more fluorine atoms, $C_1$–$C_{20}$-alkenyl, $C_1$–$C_{20}$-alkynyl, $C_1$–$C_{20}$-alkoxy, $C_1$–$C_{20}$-thioether, $C_1$–$C_{20}$-silyl, $C_1$–$C_{20}$-ester, $C_1$–$C_{20}$-amino, $C_1$–$C_{20}$-fluoroalkyl, and optionally substituted aryl or heteroaryl, A and C are optionally substituted arylene or heteroarylene, A and C are —$CX^1$=$CX^2$— or —C≡C—, in at least one monomer unit $(A)_a$—$(B)_b$—$(C)_c$ a, b and c are 1, and one of A and C is arylene or heteroarylene and the other is —$CX^1$=$CX^2$— or —C≡C—, n>1.

Especially preferred are mono-, oligo- and polymers of the following formulae

Ia

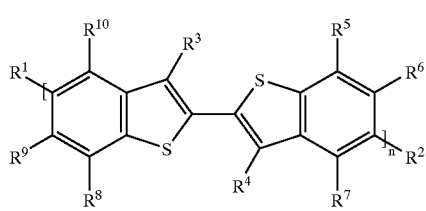

Ib

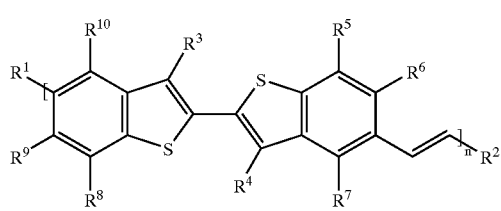

-continued
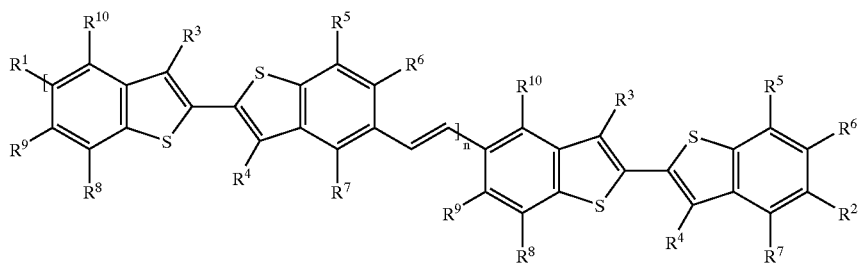 Ic
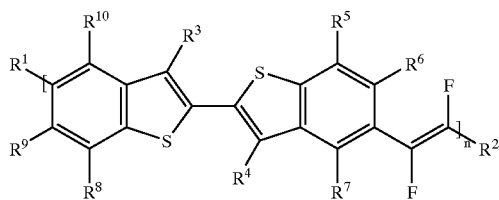 Id
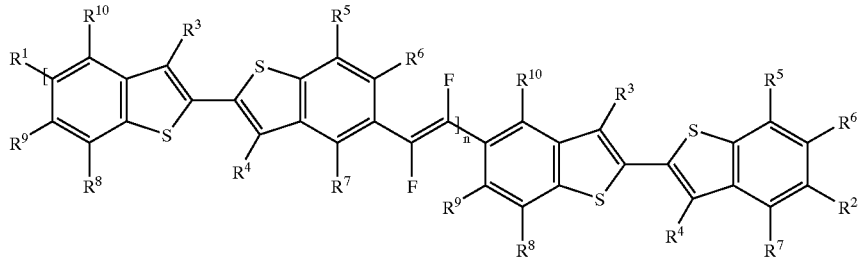 Ie
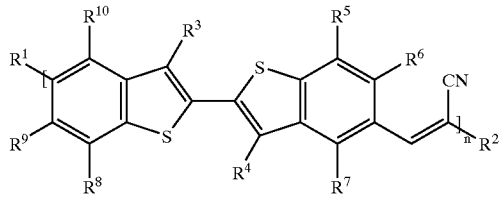 If
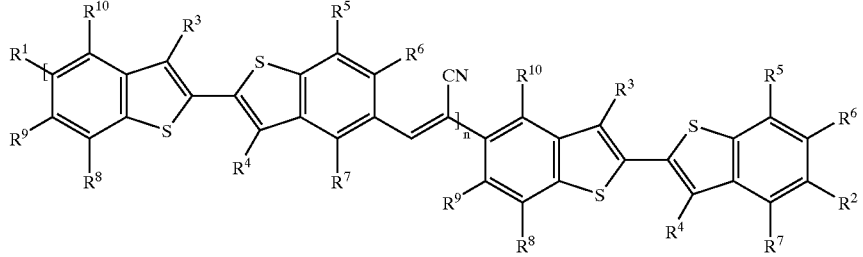 Ig
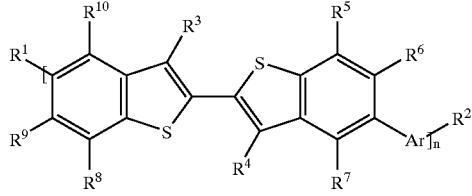 Ih
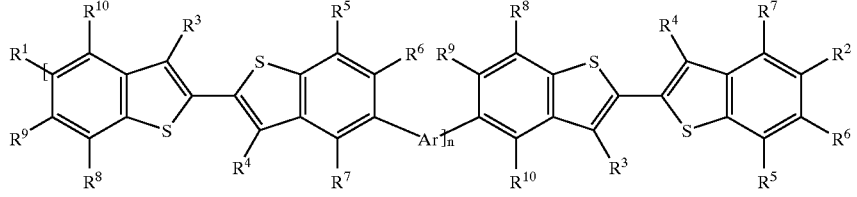 Ii

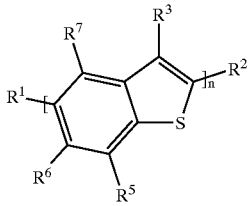

Ik

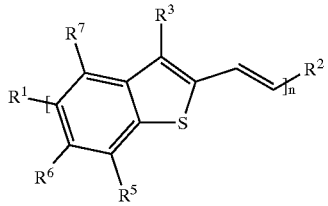

Im

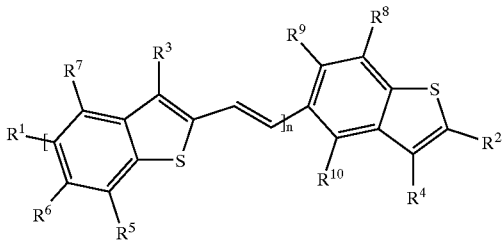

In wherein $R^1$ to $R^{10}$ have the meanings given above, Ar is arylene or heteroarylene optionally substituted, for example, by one or more of F, Cl, Br, I, CN, and straight chain, branched or cyclic alkyl having 1 to 20 C atoms, which is unsubstituted, mono- or poly-substituted by F, Cl, Br, I, —CN or —OH, and in which one or more non-adjacent CH$_2$ groups are optionally replaced, in each case independently from one another, by —O—, —S—, —NH—, —NR$^0$—, —SiR$^0$R$^{00}$—, —CO—, —COO—, OCO—, —OCO—O, —S—CO—, —CO—S—, —CH=CH— or —C≡C— in such a manner that O and/or S atoms are not linked directly to one another, and n is an integer from 1 to 5000.

Particularly preferred are oligo- and polymers of these preferred formulae wherein $R^3$ and $R^4$ are independently of each other alkyl with 1–16 C atoms that is optionally fluorinated, $R^5$ to $R^{10}$ are independently of each other H, F or alkyl with 1–16 C atoms that is optionally fluorinated, $R^1$ and $R^2$ are independently of each other H, halogen, alkyl with 1–16 C atoms that is optionally fluorinated or P—Sp—X, Ar is 1,4-phenylene, alkoxyphenylene, alkylfluorene, thiophene-2,5-diyl, thienothiophene-2,5-diyl or dithienothiophene-2,6-diyl, and n is an integer from 2 to 5000, in particular from 20 to 1000.

Further preferred are reactive monomers of the above preferred formulae, wherein n is 1 or 2, $R^3$ and $R^4$ are independently of each other alkyl with 1–16 C atoms that is optionally fluorinated, $R^5$ to $R^{10}$ are independently of each other H, F or alkyl with 1–16 C atoms that is optionally fluorinated, $R^1$ and $R^2$ are independently of each other H, halogen, alkyl with 1–16 C atoms that is optionally fluorinated or P—Sp—X, Ar is 1,4-phenylene, alkoxyphenylene, alkylfluorene, thiophene-2,5-diyl, thienothiophene-2,5-diyl or dithienothiophene-2,6-diyl, with at least one, preferably both of $R^1$ and $R^2$ denoting P—Sp—X.

Aryl and heteroaryl preferably denote a mono-, bi- or tricyclic aromatic or heteroaromatic with up to 25 C atoms, wherein the rings can be fused, and in which the heteroaromatic groups contain at least one hetero ring atom, preferably selected from N, O and S. The aryl and heteroaryl groups are optionally substituted with one or more of F, Cl, Br, I, CN, and straight chain, branched or cyclic alkyl having 1 to 20 C atoms, which is unsubstituted, mono- or poly-substituted by F, Cl, Br, I, —CN or —OH, and in which one or more non-adjacent CH$_2$ groups are optionally replaced, in each case independently from one another, by —O—, —S—, —NH—, —NR$^0$—, —SiR$^0$R$^{00}$—, —CO—, —COO—, OCO—, —OCO—O, —S—CO—, —CO—S—, —CH=CH— or —C≡C— in such a manner that O and/or S atoms are not linked directly to one another.

Especially preferred aryl and heteroaryl groups are phenyl in which, in addition, one or more CH groups may be replaced by N, naphthalene, thiophene, thienothiophene, dithienothiophene, alkyl fluorene and oxazole, all of which can be unsubstituted, mono- or polysubstituted with L, wherein L is halogen or an alkyl, alkoxy, alkylcarbonyl or alkoxycarbonyl group with 1 to 12 C atoms, wherein one or more H atoms may be replaced by F or Cl.

Arylene and heteroarylene preferably denote a mono-, bi- or tricyclic divalent aromatic or heteroaromatic radicals with up to 25 C atoms, that may also comprise condensed rings, in which the heteroaromatic groups contain at least one hetero ring atom, preferably selected from N, O and S. The arylene and heteroarylene groups are optionally substituted with one or more of F, Cl, Br, I, CN, and straight chain, branched or cyclic alkyl having 1 to 20 C atoms, which is unsubstituted, mono- or poly-substituted by F, Cl, Br, I, —CN or —OH, and in which one or more non-adjacent CH$_2$ groups are optionally replaced, in each case independently from one another, by —O—, —S—, —NH—, —NR$^0$—, —SiR$^0$R$^{00}$—, —CO—, —COO—, OCO—, —OCO—O, —S—CO—, —CO—S—, —CH=CH— or —C≡C— in such a manner that O and/or S atoms are not linked directly to one another.

Especially preferred arylene and heteroarylene groups are 1,4-phenylene in which, in addition, one or more CH groups may be replaced by N, naphthalene-2,6-diyl, thiophene-2,5-diyl, thienothiophene-2,5-diyl, dithienothiophene-2,6-diyl, alkyl fluorene and oxazole, all of which can be unsubstituted, mono- or polysubstituted with L as defined above.

$CX^1=CX^2$ is preferably —CH=CH—, —CH=CF—, —CF=CH—, —CF=CF—, —CH=C(CN)— or —C(CN)=CH—.

If in the formulae shown above and below one of $R^1$ to $R^{10}$ is an alkyl or alkoxy radical, i.e., where the terminal CH$_2$ group is replaced by —O—, this may be straight-chain or branched. It is preferably straight-chain, has 2 to 8 carbon atoms and accordingly is preferably ethyl, propyl, butyl, pentyl, hexyl, heptyl, octyl, ethoxy, propoxy, butoxy, pentoxy, hexyloxy, heptoxy, or octoxy, furthermore methyl, nonyl, decyl, undecyl, dodecyl, tridecyl, tetradecyl, pentadecyl, nonoxy, decoxy, undecoxy, dodecoxy, tridecoxy or tetradecoxy, for example.

Oxaalkyl, i.e. where one $CH_2$ group is replaced by —O—, is preferably straight-chain 2-oxapropyl (=methoxymethyl), 2-(=ethoxymethyl) or 3-oxabutyl (=2-methoxyethyl), 2-, 3-, or 4-oxapentyl, 2-, 3-, 4-, or 5-oxahexyl, 2-, 3-, 4-, 5-, or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-, 7-, 8- or 9-oxadecyl, for example.

Fluoroalkyl is preferably $C_iF_{2i+1}$, wherein i is an integer from 1 to 15, in particular $CF_3$, $C_2F_5$, $C_3F_7$, $C_4F_9$, $C_5F_{11}$, $C_6F_{13}$, $C_7F_{15}$ or $C_8F_{17}$, very preferably $C_6F_{13}$.

Halogen is preferably F or Cl.

The polymerisable or reactive group P is preferably selected from $CH_2=CW^1$—COO—,

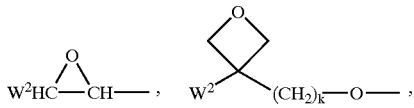

$CH_2=CW^2$—$(O)_{k1}$—, $CH_3$—CH=CH—O—, HO—$CW^2W^3$—, HS—$CW^2W^3$—, $HW^2N$—, HO—$CW^2W^3$—NH—, $CH_2=CW^1$—CO—NH—, $CH_2$=CH—$(COO)_{k1}$—Phe-$(O)_{k2}$—, Phe-CH=CH—, HOOC—, OCN— and $W^4W^5W^6Si$—, with $W^1$ being H, Cl, CN, phenyl or alkyl with 1 to 5 C-atoms, in particular H, Cl or $CH_3$, $W^2$ and $W^3$ being independently of each other H or alkyl with 1 to 5 C-atoms, in particular methyl, ethyl or n-propyl, $W^4$, $W^5$ and $W^6$ being independently of each other Cl, oxaalkyl or oxacarbonylalkyl with 1 to 5 C-atoms, Phe being 1,4-phenylene and $k_1$ and $k_2$ being independently of each other 0 or 1.

Especially preferred groups P are $CH_2$=CH—COO—, $CH_2$=C($CH_3$)—COO—, $CH_2$=CH—, $CH_2$=CH—O— and

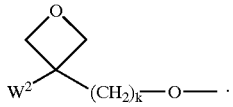

Very preferred are acrylate and oxetane groups. Oxetanes produce less shrinkage upon polymerisation (cross-linking), which results in less stress development within films, leading to higher retention of ordering and fewer defects. Oxetane cross-linking also requires cationic initiator, which unlike free radical initiator is inert to oxygen.

As for the spacer group Sp all groups can be used that are known for this purpose to those skilled in the art. The spacer group Sp is preferably a linear or branched alkylene group having 1 to 20 C atoms, in particular 1 to 12 C atoms, in which, in addition, one or more non-adjacent $CH_2$ groups may be replaced by —O—, —S—, —NH—, —N($CH_3$)—, —CO—, —O—CO—, —S—CO—, —O—COO—, —CO—S—, —CO—O—, —CH(halogen)-, —C(halogen)$_2$—, —CH(CN)—, —CH=CH— or —C≡C—, or a siloxane group.

Typical spacer groups are for example —$(CH_2)_p$—, —$(CH_2CH_2O)_r$—$CH_2CH_2$—, —$CH_2CH_2$—S—$CH_2CH_2$— or —$CH_2CH_2$—NH—$CH_2CH_2$— or —$(SiR^0R^{00}$—O$)_p$—, with p being an integer from 2 to 12, r being an integer from 1 to 3 and $R^0$ and $R^{00}$ having the meanings given in formula I.

Preferred spacer groups are ethylene, propylene, butylene, pentylene, hexylene, heptylene, octylene, nonylene, decylene, undecylene, dodecylene, octadecylene, ethyleneoxyethylene, methyleneoxybutylene, ethylene-thioethylene, ethylene-N-methyl-iminoethylene, 1-methylalkylene, ethenylene, propenylene and butenylene for example.

Further preferred are compounds with one or two groups P—Sp—X wherein Sp and/or X is a single bond.

In case of compounds with two groups P—Sp—X, each of the two polymerisable groups P, the two spacer groups Sp, and the two linkage groups X can be identical or different.

SCLCPs obtained from the inventive compounds or mixtures by polymerisation or copolymerisation have a backbone that is formed by the polymerisable group P in formula I.

The mono-, oligo- and polymers of the present invention can be synthesized according to or in analogy to known methods. Some preferred methods are described below.

Starting from the commercially available 3-bromobenzo[b]thiophene (5), a synthetic route to poly(2,2'-bisbenzo[b]thiophene) (4) is outlined below in Scheme 1. 3-bromobenzo[b]thiophene (5) is alkylated to (6) using an alkyl grignard and Ni(dppp)Cl$_2$. Benzo[b]thiophene (6) is brominated at the 2-position using n-butyllithium followed by bromine to yield (7). 2-Bromobenzo[b]thiophene (7) is homo-coupled using a liganded nickel complex reducing agent (generated from NaH, t-AmONa, Ni(OAc)$_2$ and bipyridine) to yield 2,2'-bisbenzo[b]thiophene (2). Bromination of 2,2'-bisbenzo[b]thiophene (2) with N-bromosuccinimide or bromine water yields 5–5'-dibromo 2,2'-bisbenzo[b]thiophene (8).

Poly(2,2'-bisbenzo[b]thiophene) (4) is synthesised from 5,5'-dibromo-2,2'-bisbenzo[b]thiophene (8) by one of two methods. Firstly, (8) is directly polymerised using Ni(cod)$_2$ and triphenylphosphine (Yamamoto coupling) to yield (4) [see T. Yamamoto, A. Morita, Y. Miyazaki, T. Maruyama, H. Wakayama, Z. H. Zhou, Y. Nakamura, T. Kanbara, S. Sasaki and K. Kubota, *Macromolecules*, 1992, 25, 1214]. Alternatively, (8) is converted to the mono-Grignard and polymerised using Ni(dppp)Cl$_2$ to yield (4) [see Loewe, R. S., S. M. Khersonsky, and R. D. McCullough, *Advanced Materials*, 1999. 11(3), 250–253; Loewe, R. S., et al., *Macromolecules*, 2001, 34, 4324–4337.].

Scheme 1:

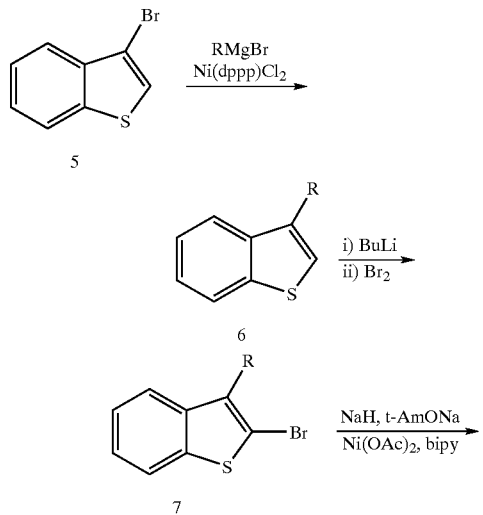

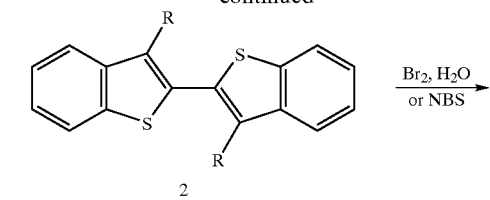

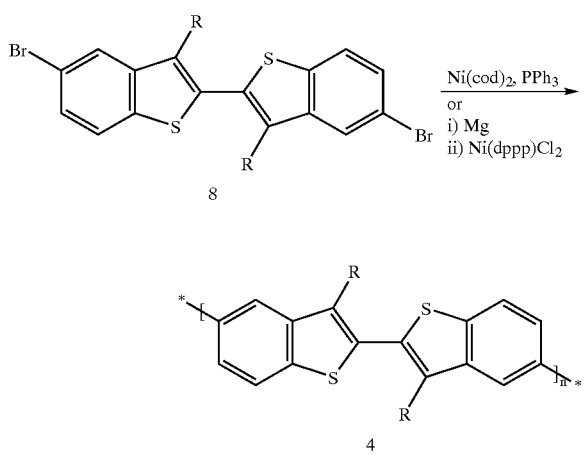

Reactive Mesogens

Compounds of formula I comprising polymerisable groups can be synthesized according to or in analogy to the following methods.

As shown in Scheme 2, 5,5'-dibromo-2,2'-bisbenzo[b]thiophene (8) can be cross-coupled with an alkyl zinc reagent in the presence of a nickel catalyst to yield (9) [see B. H. Lipshutz, P. A. Blomgren and S. K. Kim, *Tetrahedron Lett.*, 1999, 40, 2, 197].

Many organozinc reagents are commercially available or are readily prepared form the corresponding alkyl iodide. Routine methodology converts the bis-alkyl alcohol or chloride (9) into the bis-acrylate or bis-oxetane.

Scheme 2:

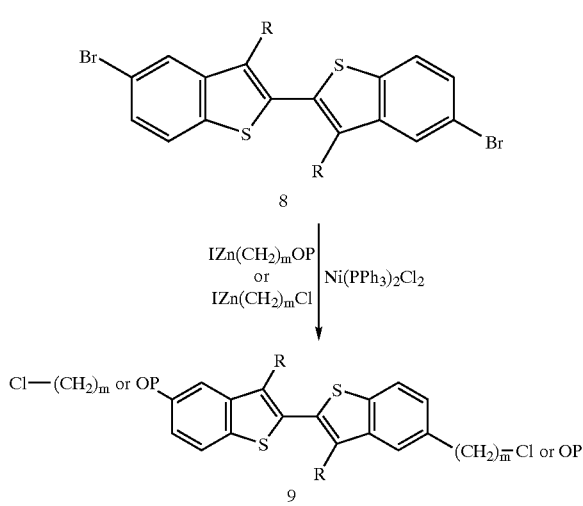

wherein m is an integer, e.g., from 1 to 20 and P is a protecting group.

Polymerisation of reactive mesogens can be carried out for example by thermal cross-linking or photoinitiated cross-linking.

Polymers Containing Conjugated Groups $CX^1=CX^2$ or Ar

The Stille coupling of dibromo 2,2'-bisbenzo[b]thiophene (8) with the bis-organotin reagent (10) as shown in Scheme 3 yields polymer (11) containing $CX^1=CX^2$ groups [see R. S. Loewe and R. D. McCullough, *Chem. Mater.*, 2000, 12, 3214.].

Scheme 3

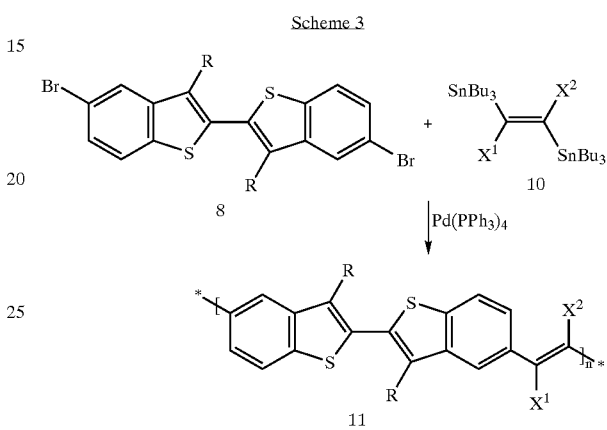

The Suzuki coupling of dibromo 2,2'-bisbenzo[b]thiophene (8) with bis-boronic acid (12) according to Scheme 4 yields polymer (13) containing aryl groups.

Scheme 4:

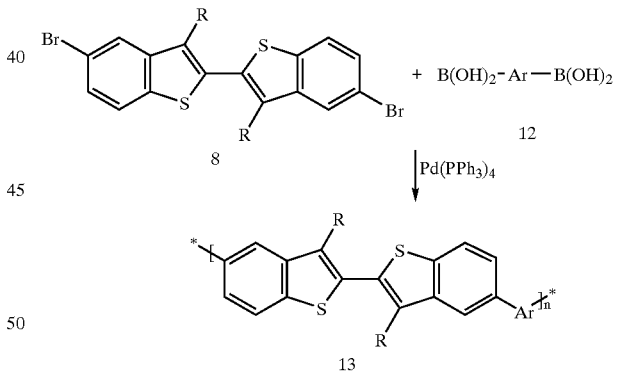

A route to poly(2,5-benzo[b]thiophene) (3) is oulined in scheme 5.

3-Alkylbenzo[b]thiophene (6) is lithiated in the 2 position by treatment with n-BuLi, and the resulting anion is reacted with iodine to afford 14. This intermediate is brominated in the 5 position by treatment with bromine to afford 15. Subsequent lithiation at the more reactive iodo group followed by treatment with $MgBr_2.OEt_2$ or $ZnCl_2$ yields the organomagnesium or organozinc intermediate respectively. Addition of a nickel catalyst followed by warming affords polymer (3).

Scheme 5:

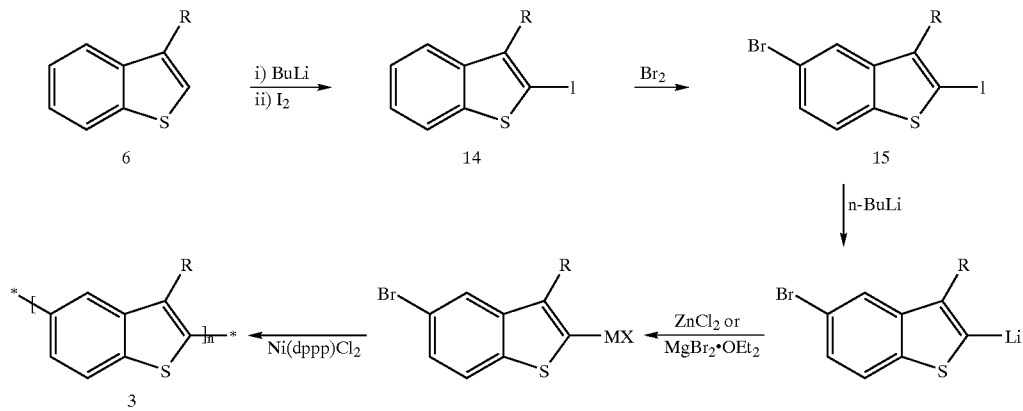

A further aspect of the invention relates to both the oxidised and reduced form of the compounds and materials according to this invention. Either loss or gain of electrons results in formation of a highly delocalised ionic form, which is of high conductivity. This can occur on exposure to common dopants. Suitable dopants and methods of doping are known to those skilled in the art, e.g. from EP 0 528 662, U.S. Pat. No. 5,198,153 or WO 96/21659.

The doping process typically implies treatment of the semiconductor material with an oxidating or reducing agent in a redox reaction to form delocalised ionic centres in the material, with the corresponding counterions derived from the applied dopants. Suitable doping methods comprise for example exposure to a doping vapor in the atmospheric pressure or at a reduced pressure, electrochemical doping in a solution containing a dopant, bringing a dopant into contact with the semiconductor material to be thermally diffused, and ion-implantantion of the dopant into the semiconductor material.

When electrons are used as carriers, suitable dopants are for example halogens (e.g., $I_2$, $Cl_2$, $Br_2$, ICl, $ICl_3$, IBr and IF), Lewis acids (e.g., $PF_5$, $AsF_5$, $SbF_5$, $BF_3$, $BCl_3$, $SbCl_5$, $BBr_3$ and $SO_3$), protonic acids, organic acids, or amino acids (e.g. HF, HCl, $HNO_3$, $H_2SO_4$, $HClO_4$, $FSO_3H$ and $ClSO_3H$), transition metal compounds (e.g. $FeCl_3$, FeOCl, $Fe(ClO_4)_3$, $Fe(4\text{-}CH_3C_6H_4SO_3)_3$, $TiCl_4$, $ZrCl_4$, $HfCl_4$, $NbF_5$, $NbCl_5$, $TaCl_5$, $MoF_5$, $MoCl_5$, $WF_5$, $WCl_6$, $UF_6$ and $LnCl_3$ (wherein Ln is a lanthanoid), anions (e.g., $Cl^-$, $Br^-$, $I^-$, $I_3^-$, $HSO_4^-$, $SO_4^{2-}$, $NO_3^-$, $ClO_4^-$, $BF_4^-$, $PF_6^-$, $AsF_6^-$, $SbF_6^-$, $FeCl_4^-$, $Fe(CN)_6^{3-}$, and anions of various sulfonic acids, such as aryl-$SO_3^-$). When holes are used as carriers, examples of dopants are cations (e.g., $H^+$, $Li^+$, $Na^+$, $K^+$, $Rb^+$ and $Cs^+$), alkali metals (e.g., Li, Na, K, Rb, and Cs), alkaline-earth metals (e.g., Ca, Sr, and Br), $O_2$, $XeOF_4$, $(NO_2^+)(SbF_6^-)$, $(NO_2^+)(SbCl_6^-)$, $(NO_2+)(BF_4^-)$, $AgClO_4$, $H_2IrCl_6$, $La(NO_3)_3 \cdot 6H_2O$, $FSO_2OOSO_2F$, Eu, acetylcholine, $R_4N^+$, (R is an alkyl group), $R_4P^+$ (R is an alkyl group), $R_6As^+$ (R is an alkyl group), and $R_3S^+$ (R is an alkyl group).

The conducting form of the compounds and materials of the present invention can be used as an organic "metal" in applications, for example, but not limited to, charge injection layers and ITO planarising layers in organic light emitting diode applications, films for flat panel displays and touch screens, antistatic films, printed conductive substrates, patterns ot tracts in electronic applications such as printed circuit boards and condensers.

A preferred embodiment of the present invention relates to mono-, oligo- and polymers of formula I that are mesogenic or liquid crystalline, and very preferably comprise one or more polymerisable groups. Very preferred materials of this type are monomers and oligomers of formula I wherein n is an integer from 1 to 15 and $R^1$ and/or $R^2$ denote P—Sp—X.

These materials are particularly useful as semiconductors or charge transport materials, as they can be aligned into uniform highly ordered orientation in their liquid crystal phase by known techniques, thus exhibiting a higher degree of order that leads to particularly high charge carrier mobility. The highly ordered liquid crystal state can be fixed by in situ polymerisation or crosslinking via the groups P to yield polymer films with high charge carrier mobility and high thermal, mechanical and chemical stability.

It is also possible to copolymerise the polymerisable mono-, oligo- and polymers according to the present invention with other polymerisable mesogenic or liquid crystal monomers that are known from prior art, in order to induce or enhance liquid crystal phase behaviour.

Thus, another object of the invention is a polymerisable liquid crystal material comprising one or more mono-, oligo- or polymers of the present invention as described above and comprising at least one polymerisable group, and optionally comprising one or more further polymerisable compounds, wherein at least one of the polymerisable mono-, oligo- and polymers of the present invention and/or the further polymerisable compounds is mesogenic or liquid crystalline.

Particularly preferred are liquid crystal materials having a nematic and/or smectic phase. For FET applications smectic materials are especially preferred. For OLED applications nematic or smectic materials are especially preferred.

Another object of the present invention is an anisotropic polymer film with charge transport properties obtainable from a polymerisable liquid crystal material as defined above that is aligned in its liquid crystal phase into macroscopically uniform orientation and polymerised or crosslinked to fix the oriented state.

Another object of the invention is a liquid crystal side chain polymer (SCLCP) obtained from a polymerisable liquid crystal material as defined above by polymerisation or polymeranaloguous reaction. Particularly preferred are SCLCPs obtained from one or more monomers according to formula I wherein one or both of $R^1$ and $R^2$ are a polymerisable or reactive group, or from a polymerisable mixture comprising one or more of such monomers of formula I.

Another object of the invention is an SCLCP obtained from one or more monomers of formula I wherein one or both of $R^1$ and $R^2$ are a polymerisable group, or from a polymerisable liquid crystal mixture as defined above, by copolymerisation or polymeranaloguous reaction together with one or more additional mesogenic or non-mesogenic comonomers.

Side chain liquid crystal polymers or copolymers (SCLCPs), in which the semiconducting component is located as a pendant group, separated from a flexible backbone by an aliphatic spacer group, offer the possibility to obtain a highly ordered lamellar like morphology. This structure consists of closely packed conjugated aromatic mesogens, in which very close (typically <4 Å) pi—pi stacking can occur. This stacking allows intermolecular charge transport to occur more easily, leading to high charge carrier mobilities. SCLCPs are advantageous for specific applications as they can be readily synthesized before processing and then e.g. be processed from solution in an organic solvent. If SCLCPs are used in solutions, they can orient spontaneously when coated onto an appropriate surface and when at their mesophase temperature, which can result in large area, highly ordered domains.

Polymerisation is preferably carried out by in-situ polymerisation of a coated layer of the material, preferably during fabrication of the electronic or optical device comprising the inventive semiconductor material. In case of liquid crystal materials, these are preferably aligned in their liquid crystal state into homeotropic orientation prior to polymerisation, where the conjugated pi-electron systems are orthogonal to the direction of charge transport. This ensures that the intermolecular distances are minimised and hence then energy required to transport charge between molecules is minimised. The molecules are then polymerised or crosslinked to fix the uniform orientation of the liquid crystal state. Alignment and curing are carried out in the liquid crystal phase or mesophase of the material. This technique is known in the art and is generally described for example in D. J. Broer, et al., Angew. Makromol. Chem. 183, (1990), 45–66

Alignment of the liquid crystal material can be achieved for example by treatment of the substrate onto which the material is coated, by shearing the material during or after coating, by application of a magnetic or electric field to the coated material, or by the addition of surface-active compounds to the liquid crystal material. Reviews of alignment techniques are given for example by I. Sage in "Thermotropic Liquid Crystals", edited by G. W. Gray, John Wiley & Sons, 1987, pages 75–77, and by T. Uchida and H. Seki in "Liquid Crystals—Applications and Uses Vol. 3", edited by B. Bahadur, World Scientific Publishing, Singapore 1992, pages 1–63. A review of alignment materials and techniques is given by J. Cognard, Mol. Cryst. Liq. Cryst. 78, Supplement 1 (1981), pages 1–77.

Polymerisation takes place by exposure to heat or actinic radiation. Actinic radiation means irradiation with light, like UV light, IR light or visible light, irradiation with X-rays or gamma rays or irradiation with high energy particles, such as ions or electrons. Preferably polymerisation is carried out by UV irradiation at a non-absorbing wavelength. As a source for actinic radiation for example a single UV lamp or a set of UV lamps can be used. When using a high lamp power the curing time can be reduced. Another possible source for actinic radiation is a laser, like, e.g., a UV laser, an IR laser or a visible laser.

Polymerisation is preferably carried out in the presence of an initiator absorbing at the wavelength of the actinic radiation. For example, when polymerising by means of UV light, a photoinitiator can be used that decomposes under UV irradiation to produce free radicals or ions that start the polymerisation reaction. When curing polymerisable materials with acrylate or methacrylate groups, preferably a radical photoinitiator is used, when curing polymerisable materials with vinyl, epoxide and oxetane groups, preferably a cationic photoinitiator is used. It is also possible to use a polymerisation initiator that decomposes when heated to produce free radicals or ions that start the polymerisation. As a photoinitiator for radical polymerisation for example the commercially available Irgacure 651, Irgacure 184, Darocure 1173 or Darocure 4205 (all from Ciba Geigy AG) can be used, whereas in case of cationic photopolymerisation the commercially available UVI 6974 (Union Carbide) can be used.

The polymerisable material can additionally comprise one or more other suitable components such as, for example, catalysts, sensitizers, stabilizers, inhibitors, chain-transfer agents, co-reacting monomers, surface-active compounds, lubricating agents, wetting agents, dispersing agents, hydrophobing agents, adhesive agents, flow improvers, defoaming agents, deaerators, diluents, reactive diluents, auxiliaries, colourants, dyes or pigments.

Mono-, oligo- and polymers comprising one or more groups P—Sp—X can also be copolymerised with polymerisable mesogenic compounds to induce, or, in case of mesogenic materials of formula I, enhance liquid crystal phase behaviour. Polymerisable mesogenic compounds that are suitable as comonomers are known in prior art and disclosed for example in WO 93/22397; EP 0,261,712; DE 195,04,224; WO 95/22586 and WO 97/00600.

SCLCPs can be prepared from the polymerisable compounds or mixtures according to the invention by the methods described above, or by conventional polymerisation techniques which are known to those skilled in the art, including for example radicalic, anionic or cationic chain polymerisation, polyaddition or polycondensation. Polymerisation can be carried out for example as polymerisation in solution, without the need of coating and prior alignment, or polymerisation in situ. It is also possible to form SCLCPs by grafting compounds according to the invention with a suitable reactive group, or mixtures thereof, to presynthesized isotropic or anisotropic polymer backbones in a polymeranaloguous reaction. For example, compounds with a terminal hydroxy group can be attached to polymer backbones with lateral carboxylic acid or ester groups, compounds with terminal isocyanate groups can be added to backbones with free hydroxy groups, compounds with terminal vinyl or vinyloxy groups can be added, e.g., to polysiloxane backbones with Si—H groups. It is also possible to form SCLCPs by copolymerisation or polymeranaloguous reaction from the inventive compounds together with conventional mesogenic or non mesogenic comonomers. Suitable comonomers are known to those skilled in the art. In principle it is possible to use all conventional comonomers known in the art that carry a reactive or polymerisable group capable of undergoing the desired polymer-forming reaction, like for example a polymerisable or reactive group P as defined above. Typical mesogenic comonomers are for example those mentioned in WO 93/22397; EP 0,261,712; DE 195,04,224; WO 95/22586 and WO 97/00600. Typical non mesogenic comonomers are for example alkyl mono- or diacrylates or alkyl mono- or dimethacrylates with alkyl groups of 1 to 20 C atoms, like methyl acrylate or methyl methacrylate, trimethylpropane trimethacrylate or pentaerythritol tetraacrylate.

The mono-, oligo- and polymers of the present invention are useful as optical, electronic and semiconductor materials, in particular as charge transport materials in field effect transistors (FETs), e.g., as components of integrated circuitry, ID tags or TFT applications. Alternatively, they may be used in organic light emitting diodes (OLEDs) in electroluminescent display applications or as backlight of, e.g., liquid crystal displays, as photovoltaics or sensor materials, for electrophotographic recording, and for other semiconductor applications.

Especially the oligomers and polymers according to the invention show advantageous solubility properties which allow production processes using solutions of these compounds. Thus films, including layers and coatings, may be generated by low cost production techniques, e.g., spin coating. Suitable solvents or solvent mixtures comprise alkanes and/or aromatics, especially their fluorinated derivatives.

The materials of the present invention are useful as optical, electronic and semiconductor materials, in particular as charge transport materials in field effect transistors (FETs), as photovoltaics or sensor materials, for electrophotographic recording, and for other semiconductor applications. Such FETs, where an organic semiconductive material is arranged as a film between a gate-dielectric and a drain and a source electrode, are generally known, e.g., from U.S. Pat. No. 5,892,244, WO 00/79617, U.S. Pat. No. 5,998,804, and from the references cited in the background and prior art chapter and listed below. Due to the advantages, like low cost production using the solubility properties of the compounds according to the invention and thus the processibility of large surfaces, preferred applications of these FETs are such as integrated circuitry, TFT-displays and security applications.

In security applications, field effect transistors and other devices with semiconductive materials, like transistors or diodes, may be used for ID tags or security markings to authenticate and prevent counterfeiting of documents of value like banknotes, credit cards or ID cards, national ID documents, licenses or any product with money value, like stamps, tickets, shares, cheques, etc.

Alternatively, the mono-, oligo- and polymers according to the invention may be used in organic light emitting devices or diodes (OLEDs), e.g., in display applications or as backlight of e.g. liquid crystal displays. Common OLEDs are realized using multilayer structures. An emission layer is generally sandwiched between one or more electron-transport and/or hole-transport layers. By applying an electric voltage electrons and holes as charge carriers move towards the emission layer where their recombination leads to the excitation and hence luminescence of the lumophor units contained in the emission layer. The inventive compounds, materials and films may be employed in one or more of the charge transport layers and/or in the emission layer, corresponding to their electrical and/or optical properties. Furthermore their use within the emission layer is especially advantageous, if the compounds, materials and films according to the invention show electroluminescent properties themselves or comprise electroluminescent groups or compounds. The selection, characterization as well as the processing of suitable monomeric, oligomeric and polymeric compounds or materials for the use in OLEDs is generally known by a person skilled in the art, see, e.g., Meerholz, Synthetic Materials, 111–112, 2000, 31–34, Alcala, J. Appl. Phys., 88, 2000, 7124–7128 and the literature cited therein.

According to another use, the inventive compounds, materials or films, especially those which show photoluminescent properties, may be employed as materials of light sources, e.g., of display devices such as described in EP 0 889 350 A1 or by C. Weder et al., Science, 279, 1998, 835–837.

The entire disclosure of all applications, patents and publications, cited above and below, and of corresponding European Patent Application No. 01123509.0, filed Sep. 29, 2001, is hereby incorporated by reference.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A compound according to formula I

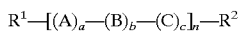

$$R^1\text{—}[(A)_a\text{—}(B)_b\text{—}(C)_c]_n\text{—}R^2 \quad\quad I$$

wherein

A and C are independently of each other —CX¹=CX²—, —C≡C—, or optionally substituted arylene or heteroarylene, X¹ and X² are independently of each other H, F, Cl or CN, B is 2,5-benzo[b]thiophene or 2,2'-bisbenzo[b]thiophene that is optionally substituted with one or more groups R, R is, in each case independently, H, halogen, optionally substituted aryl, optionally substituted heteroaryl, or straight chain, branched or cyclic alkyl with 1 to 20 C-atoms, which is unsubstituted, or mono- or poly-substituted by F, Cl, Br, I or CN, wherein one or more non-adjacent CH₂ groups can optionally be replaced, in each case independently from one another, by —O—, —S—, —NH—, —NR⁰—, —SiR⁰R⁰⁰—, —SnR⁰R⁰⁰—, —CO—, —COO—, —OCO—, —OCO—O—, —S—CO—, —CO—S—, —CH=CH— or —C≡C— in such a manner that O and/or S atoms are not linked directly to one another, or R can be P—Sp—X, R¹ and R² are independently of each other H, halogen, optionally substituted aryl, optionally substituted heteroaryl, or straight chain, branched or cyclic alkyl with 1 to 20 C-atoms, which is unsubstituted, or mono- or poly-substituted by F, Cl, Br, I or CN, wherein one or more non-adjacent CH₂ groups can optionally be replaced, in each case independently from one another, by —O—, —S—, —NH—, —NR⁰—, —SiR⁰R⁰⁰—, —SnR⁰R⁰⁰—, —CO—, —COO—, —OCO—, —OCO—O—, —S—CO—, —CO—S—, —CH=CH— or —C≡C— in such a manner that O and/or S atoms are not linked directly to one another, or R¹ and R² can each independently be P—Sp—X, R⁰, R⁰⁰ are independently of each other H or alkyl with 1 to 12 C-atoms, P is a polymerisable or reactive group, Sp is a spacer group or a single bond, and X is —O—, —S—, —OCH₂—, —CH₂O—, —CO—, —COO—, —OCO—, —OCO—O—, —CO—NR⁰—, —NR⁰—CO—, —OCH₂—, —CH₂O—, —SCH₂—, —CH₂S—, —CH=CH—COO—, —OOC—CH=CH— or a single bond, a, b, c are independently of each other 0 or 1, with a+b+c>0, and wherein in at least one recurring unit [(A)ₐ—(B)ᵦ—(C)ᵧ] b is 1, and n is an integer ≧1, wherein the recurring units [(A)ₐ—(B)ᵦ—(C)ᵧ] can be identical or different, with the proviso that in case n is 1 and a and c are 0, at least one of R, $R^1$ and $R^2$ is P—Sp—X.

2. A compound according to claim 1, wherein B is selected of the following formulae

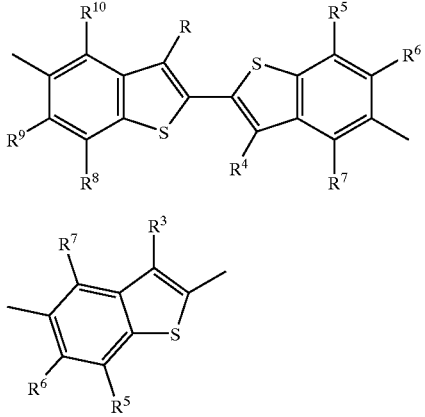

IIa

IIb wherein $R^3$ to $R^{10}$ are independently of each other H, halogen, optionally substituted aryl, optionally substituted heteroaryl, or straight chain, branched or cyclic alkyl with 1 to 20 C-atoms, which is unsubstituted, or mono- or poly-substituted by F, Cl, Br, I or CN, wherein one or more non-adjacent $CH_2$ groups can optionally be replaced, in each case independently from one another, by —O—, —S—, —NH—, —NR°—, —SiR°R°°—, —SnR°R°°—, —CO—, —COO—, —OCO—, —OCO—O—, —S—CO—, —CO—S—, —CH=CH— or —C≡C— in such a manner that O and/or S atoms are not linked directly to one another, or $R^3$ to $R^{10}$ can each independently be P—Sp—X.

3. A compound according to claim 2, wherein n is an integer from 1 to 5000.

4. A compound according to claim 2, wherein $R^3$ to $R^{10}$ are, independently of each other, $C_1$-$C_{20}$-alkyl that is optionally substituted with one or more fluorine atoms, $C_1$-$C_{20}$-alkenyl, $C_1$-$C_{20}$-alkynyl, $C_1$-$C_{20}$-alkoxy, $C_1$-$C_{20}$-thioether, $C_1$-$C_{20}$-silyl, $C_1$-$C_{20}$-ester, $C_1$-$C_{20}$-amino, $C_1$-$C_{20}$-fluoroalkyl, or optionally substituted aryl or heteroaryl.

5. A compound according to claim 4, wherein $R^3$ and $R^4$ are, independently of each other, $C_1$-$C_{20}$-alkyl that is optionally substituted with one or more fluorine atoms, $C_1$-$C_{20}$-alkenyl, $C_1$-$C_{20}$-alkynyl, $C_1$-$C_{20}$-alkoxy, $C_1$-$C_{20}$-thioether, $C_1$-$C_{20}$-silyl, $C_1$-$C_{20}$-ester, $C_1$-$C_{20}$-amino, $C_1$-$C_{20}$-fluoroalkyl, or optionally substituted aryl or heteroaryl, and $R^5$ to $R^{10}$ are H.

6. A compound according to claim 1, wherein n is an integer from 1 to 5000.

7. A compound according to claim 1, wherein n is an integer from 1 to 15 and one or both of $R^1$ and $R^2$ denote P—Sp—X.

8. A compound according to claim 1, wherein n is an integer from 2 to 5000.

9. A compound according to claim 1, wherein

P is selected from $CH_2=CW^1$—COO—,

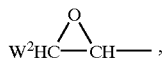

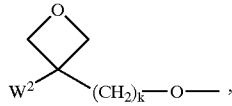

$CH_2=CW^2$—$(O)_{k1}$—, $CH_3$—CH=CH—O—, HO—$CW^2W^3$—, HS—$CW^2W^3$—, $HW^2N$—, HO—$CW^2W^3$—NH—, $CH_2=CW^1$—CO—NH—, $CH_2$=CH—$(COO)_{k1}$—Phe—$(O)_{k2}$—, Phe—CH=CH—, HOOC—, OCN— and $W^4W^5W^6Si$—, $W^1$ is H, Cl, CN, phenyl or alkyl with 1 to 5 C-atoms, $W^2$ and $W^3$ are independently of each other H or alkyl with 1 to 5 C-atoms, $W^4$, $W^5$ and $W^6$ are independently of each other Cl, oxaalkyl or oxacarbonylalkyl with 1 to 5 C-atoms, Phe is 1,4-phenylene, and $k_1$ and $k_2$ are independently of each other 0 or 1.

10. A compound according to claim 9, wherein Sp is a single bond a linear or branched alkylene group having 1 to 20 C atoms, in which, in addition, one or more non-adjacent $CH_2$ groups can optionally be replaced by —O—, —S—, —NH—, —N($CH_3$)—, —CO—, —O—CO—, —S—CO—, —O—COO—, —CO—S—, —CO—O—, —CH(halogen)-, —C(halogen)$_2$, —CH(CN)—, —CH=CH— or —C≡C—, or a siloxane group.

11. A compound according to claim 10, wherein $R^1$ to $R^{10}$ are, independently of each other, $C_1$-$C_{20}$-alkyl that is optionally substituted with one or more fluorine atoms, $C_1$-$C_{20}$-alkenyl, $C_1$-$C_{20}$-alkynyl, $C_1$-$C_{20}$-alkoxy, $C_1$-$C_{20}$-thioether, $C_1$-$C_{20}$-silyl, $C_1$-$C_{20}$-ester, $C_1$-$C_{20}$-amino, $C_1$-$C_{20}$-fluoroalkyl, or optionally substituted aryl or heteroaryl.

12. A compound according to claim 10, wherein B is selected of the following formulae

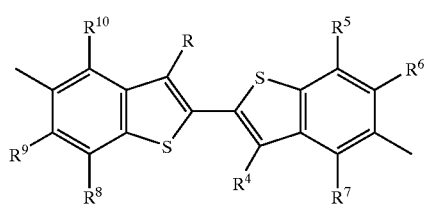

IIa

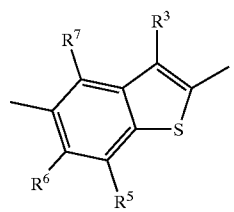

IIb wherein $R^3$ to $R^{10}$ are independently of each other H, halogen, optionally substituted aryl, optionally substituted heteroaryl, or straight chain, branched or cyclic alkyl with 1 to 20 C-atoms, which is unsubstituted, or mono- or poly-substituted by F, Cl, Br, I or CN, wherein one or more non-adjacent $CH_2$ groups can optionally be replaced, in each case independently from one another, by —O—, —S—, —NH—, —NR⁰—, —SiR⁰R⁰⁰—, —SnR⁰R⁰⁰—, —CO—, —COO—, —OCO—, —OCO—O—, —S—CO—, —CO—S—, —CH=CH— or —C≡C— in such a manner that O and/or S atoms are not linked directly to one another, or $R^3$ to $R^{10}$ can each independently be P—Sp—X.

13. A compound according to claim 1, wherein Sp is a single bond a linear or branched alkylene group having 1 to 20 C atoms, in which, in addition, one or more non-adjacent $CH_2$ groups can optionally be replaced by —O—, —S—, —NH—, —N(CH₃)—, —CO—, —O—CO—, —S—CO—, —O—COO—, —CO—S—, —CO—O—, —CH(halogen)-, —C(halogen)₂, —CH(CN)—, —CH=CH— or —C≡C—, or a siloxane group.

14. A compound according to claim 1, selected from the following formulae

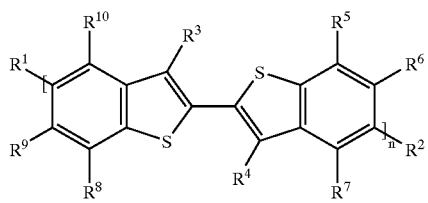

Ia

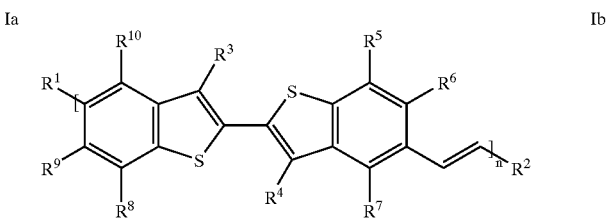

Ib

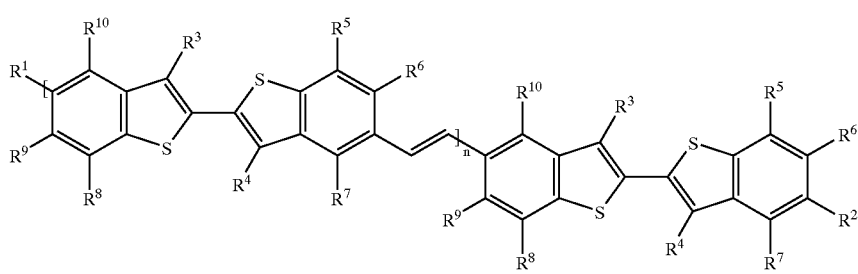

Ic

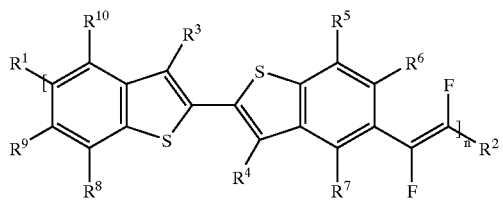

Id

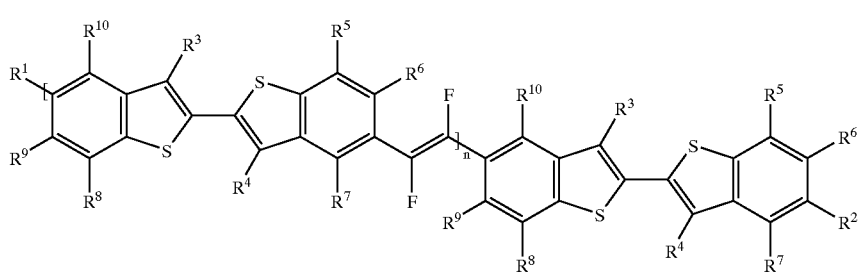

Ie

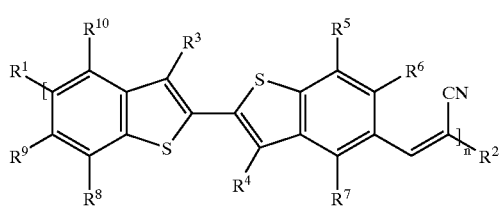

If

-continued

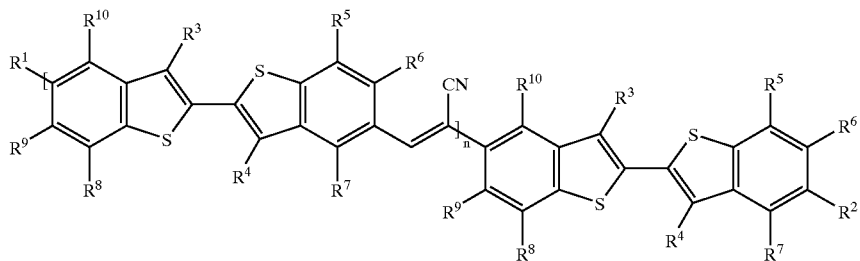

Ig

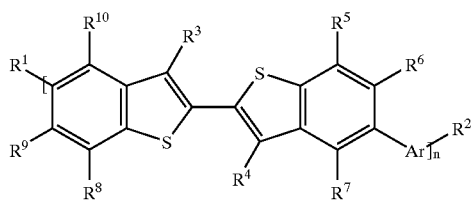

Ih

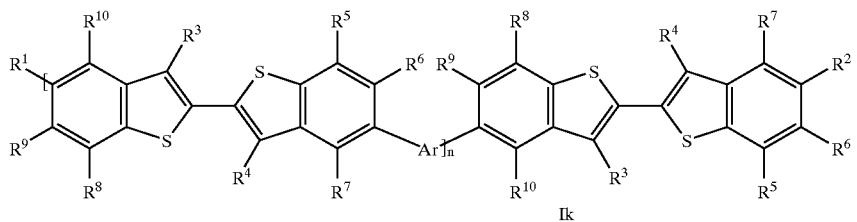

Ii

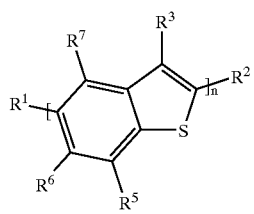

Im

Ik

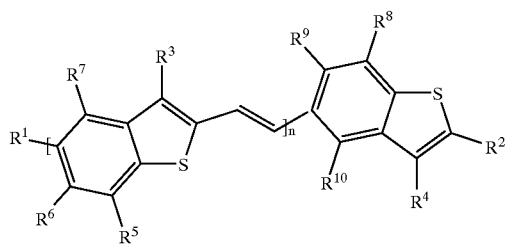

In wherein
$R^1$ to $R^{10}$ are each, independently of each other, H, halogen, optionally substituted aryl, optionally substituted heteroaryl, or straight chain, branched or cyclic alkyl with 1 to 20 C-atoms, which is unsubstituted, or mono- or poly-substituted by F, Cl, Br, I or CN, wherein one or more non-adjacent CH$_2$ groups can optionally be replaced, in each case independently from one another, by —O—, —S—, —NH—, —NR$^o$—, —SiR$^o$R$^{oo}$—, —SnR$^o$R$^{oo}$—, —CO—, —COO—, —OCO—, —OCO—O—, —S—CO—, —CO—S—, —CH═CH— or —C≡C— in such a manner that O and/or S atoms are not linked directly to one another, or one or more of $R^1$ to $R^{10}$ can be P—Sp—X, Ar is arylene or heteroarylene which is optionally substituted by one or more of F, Cl, Br, I, CN, and straight chain, branched or cyclic alkyl having 1 to 20 C atoms, which is unsubstituted, mono- or poly-substituted by F, Cl, Br, I, —CN or —OH, and in which one or more non-adjacent CH$_2$ groups are optionally replaced, in each case independently from one another, by —O—, —S—, —NH—, —NR$^o$—, —SiR$^o$R$^{oo}$—, —CO—, —COO—, OCO—, —OCO—O, —S—CO—, —CO—S—, —CH═CH— or —C≡C— in such a manner that O and/or S atoms are not linked directly to one another, and n is an integer from 1 to 5000.

15. A polymerisable liquid crystal material comprising one or more compounds of claim 1 having at least one polymerisable group, and optionally one or more further polymerisable compounds, wherein at least one of said compounds of claim 1 and/or said further polymerisable compounds is mesogenic or liquid crystalline.

16. An anisotropic polymer film with charge transport properties obtainable from a polymerisable liquid crystal material according to claim 15 that is aligned in its liquid crystal phase into macroscopically uniform orientation and polymerised or crosslinked to fix the oriented state.

17. A side chain liquid crystal polymer obtained by polymerisation of a polymerisable material of claim 16 or by grafting a polymerisable material of claim 16 to a polymer backbone in a polymeranaloguous reaction, optionally with one or more additional mesogenic or non-mesogenic comonomers.

18. In an optical, electrooptical or electronic device, like for example components of integrated circuitry, field effect transistors (FET) for example as thin film transistors in flat panel display applications or for Radio Frequency Identification (RFID) tags, or in semiconducting components for organic light emitting diode (OLED) applications such as electroluminescent displays or backlights of, e.g., liquid crystal displays, for photovoltaic or sensor devices, as electrode materials in batteries, as photoconductors and for electrophotographic applications like electrophotographic recording, the improvement wherein a polymerizable material according to claim 15 is used as a semiconductor or charge transport material.

19. In a field effect transistor, for example as a component of integrated circuitry, as a thin film transistor in flat panel display applications, or in a Radio Frequency Identification (RFID) tag, the improvement wherein a polymerizable material according to claim 15 is employed.

20. In a security marking or device, the improvement wherein said security marking or device comprises a polymerizable material according to claim 15.

21. In an optical, electrooptical or electronic device, like for example components of integrated circuitry, field effect transistors (FET) for example as thin film transistors in flat panel display applications or for Radio Frequency Identification (RFID) tags, or in semiconducting components for organic light emitting diode (OLED) applications such as electroluminescent displays or backlights of, e.g., liquid crystal displays, for photovoltaic or sensor devices, as electrode materials in batteries, as photoconductors and for electrophotographic applications like electrophotographic recording, the improvement wherein one or more compounds according to claim 1 are used as a semiconductor or charge transport material.

22. A side chain liquid crystal polymer obtained by polymerisation of one or more mono- or oligomers of claim 1 or by grafting one or more mono- or oligomers of claim 1 to a polymer backbone in a polymeranaloguous reaction, optionally with one or more additional mesogenic or non-mesogenic comonomers.

23. In an optical, electrooptical or electronic device, like for example components of integrated circuitry, field effect transistors (FET) for example as thin film transistors in flat panel display applications or for Radio Frequency Identification (RFID) tags, or in semiconducting components for organic light emitting diode (OLED) applications such as electroluminescent displays or backlights of, e.g., liquid crystal displays, for photovoltaic or sensor devices, as electrode materials in batteries, as photoconductors and for electrophotographic applications like electrophotographic recording, the improvement wherein a polymer according to claim 22 is used as a semiconductor or charge transport material.

24. In a field effect transistor, for example as a component of integrated circuitry, as a thin film transistor in flat panel display applications, or in a Radio Frequency Identification (RFID) tag, the improvement wherein one or more polymers according to claim 22 are employed.

25. In a security marking or device, the improvement wherein said security marking or device comprises one or more polymers according to claim 22.

26. In a field effect transistor, for example as a component of integrated circuitry, as a thin film transistor in flat panel display applications, or in a Radio Frequency Identification (RFID) tag, the improvement wherein one or more compounds according to claim 1 are employed.

27. In a security marking or device, the improvement wherein said security marking or device comprises a FET or RFID tag according to claim 26.

28. In a security marking or device, the improvement wherein said security marking or device comprises one or more compounds according to claim 1.

29. A compound according to claim 1 which is oxidatively or reductively doped to form conducting ionic species.

30. In a charge injection layer, planarising layer, antistatic film or conducting substrate or pattern for electronic applications or flat panel displays, the improvement wherein a compound according to claim 29 is utilized.

* * * * *